US006215027B1

(12) United States Patent
Papavassiliou et al.

(10) Patent No.: US 6,215,027 B1
(45) Date of Patent: Apr. 10, 2001

(54) BALLAST GAS USE IN LIQUID PHASE OXIDATION

(75) Inventors: Vasilis Papavassiliou, Carmel, NY (US); William Robert Williams, New Fairfield, CT (US); Matthew Lincoln Wagner, White Plains, NY (US)

(73) Assignee: Praxair Technology, Inc., Danbury, CT (US)

( * ) Notice: Subject to any disclaimer, the term of this patent is extended or adjusted under 35 U.S.C. 154(b) by 0 days.

(21) Appl. No.: 09/175,428

(22) Filed: Oct. 20, 1998

(51) Int. Cl.⁷ .................................................. C07C 45/27
(52) U.S. Cl. ............................................. 568/357; 568/836
(58) Field of Search ..................... 568/357, 358, 568/577, 836, 837; 562/406; 423/584, 582, 588

(56) References Cited

U.S. PATENT DOCUMENTS

| | | | |
|---|---|---|---|
| 3,119,837 | 1/1964 | Kingsley et al. | 260/348.5 |
| 3,855,280 | 12/1974 | Severs, Jr. | 260/497 |
| 5,183,933 | 2/1993 | Harper et al. | 562/414 |
| 5,430,181 | 7/1995 | Arpentinier et al. | 562/406 |
| 5,552,131 | 9/1996 | Jubin, Jr. | 423/584 |
| 5,693,856 | 12/1997 | Ramachandran et al. | 562/414 |
| 5,780,683 | 7/1998 | Greene et al. | 568/358 |

FOREIGN PATENT DOCUMENTS

| | | |
|---|---|---|
| 0361372 | 9/1989 | (EP) . |
| 0673910A1 | 9/1995 | (EP) . |
| 0999549A2 | 4/2000 | (EP) . |
| 0995490A3 | 7/2000 | (EP) . |
| 2410504 | 6/1979 | (FR) . |
| WO9832725 | 7/1998 | (WO) . |

OTHER PUBLICATIONS

Crescitelli et al, "On The Flammability Limits of Saturated Vapours O Hydrocarbons", *Journal of Hazardous Materials*, 5 (1982) 177–187.

T.K. Subramaniam et al, "Engineering Practice, Predict Safe Oxygen In" *Chemical Engineering*, Dec. 1989.

James G. Hansel et al, "Predicting and Controlling Flammability of Multiple Fuel and Multiple Inert Mixtures", *Plant/Operations Progress* (vol. 11, No. 4), 1991.

Roby et al, "Oxidize safely with pure oxygen", *Chemtech*, vol. 27, No. 1, pp. 39–46, 1996.

*Primary Examiner*—Sreeni Padmanabhan
(74) *Attorney, Agent, or Firm*—Bernard Lau

(57) ABSTRACT

The amount of a ballast gas needed, to prevent combustion, deflagration, and/or detonations during a liquid phase reaction of molecular oxygen and a flammable process liquid, is reduced by using a ballast gas other than nitrogen. The ballast gas is selected to have a boiling point lower than the boiling point of the flammable process liquid and selected to produce a higher limiting oxygen value (LOV) in a mixture with the flammable process liquid vapor and molecular oxygen than the LOV for the corresponding mixture substituting just nitrogen for the inerting gas.

20 Claims, 5 Drawing Sheets

BALLAST GAS USE IN LIQUID PHASE OXIDATION

BACKGROUND OF THE INVENTION

1. Field of the Invention

This invention relates generally to the vapor composition in a reactor used for carrying out a liquid phase reaction involving molecular oxygen. In particular, the invention relates to minimizing the inert gas flow supplied to a liquid phase oxidation reactor in order to prevent combustion, deflagration, or detonation in the liquid phase oxidation reactor headspace.

2. Related Background Art

Air-based, as well as oxygen-based, oxidation reactions involving flammable liquids require that the vapor or gas space above the liquid (the reactor headspace) be maintained outside the flammability range. Air-based reactions utilize molecular oxygen from an atmospheric composition, by volume percent, of gases. The atmospheric composition (air) may be at a different pressure than atmospheric pressure. Oxygen-based reactions utilize molecular oxygen from a substantially pure oxygen gas.

In oxygen-based liquid phase oxidation reactions, supplemental nitrogen is typically fed to the headspace in order to maintain the concentration of its components outside the flammability limits; in the absence of nitrogen and if the vapor pressure of the flammable liquid is in the proper range, it would be possible for vapor bubbles to enter the reactor headspace having a flammable composition.

In air-based liquid phase oxidation processes the reactor is typically designed to consume enough gaseous oxygen so that the remaining oxygen concentration is below the limiting oxygen value (LOV) for flammability. Ballast gases other than nitrogen have been described for oxidation reactions that are carried out in the gas phase. U.S. Pat. No. 3,855,280, for example, describes using methane or ethane diluents in the gas phase oxidation of ethylene and acetic acid gas to prepare vinyl acetate. European Patent No. 361,372 describes using alkanes, carbon dioxide, steam or other diluents in the gas phase production of methacrolein and methacrylic acid. U.S. Pat. No. 3,119,837 describes using methane, nitrogen, carbon dioxide, or steam in the gas phase oxidation of ethylene to form ethylene oxide.

These teachings from gas phase oxidation processes, however, cannot be extended to liquid phase oxidation processes because the liquid phase reactions present significant differences with respect to their oxidation reactions carried out in the gas phase.

One difference is related to the fact that liquid phase oxidation processes typically involve a step of recondensing a process liquid such as the reaction solvent. Accordingly, if a ballast gas other than nitrogen is used in the liquid phase process, the effects of the condensation step must be considered. Another difference is that, in contrast to gas phase oxidation processes, no heat transfer benefit is realized in the liquid phase oxidation reaction with respect to the choice of a particular inerting gas.

While the flammability of the gas phase reaction mixture depends essentially on its components, flammability in the liquid phase reactor is typically a function of temperature, pressure and on the physical properties of the flammable process liquid, often the solvent.

Furthermore, whereas in a gas phase oxidation reactor it must be ensured that the reactor composition is outside the flammability regime at every point in the reactor, only the reactor headspace raises similar concerns for a liquid phase oxidation process.

U.S. Pat. No. 5,430,181 mentions the possibility of adding a third gas such as methane, ethane or helium to liquid phase oxidations but does not provide any detail on how this may be accomplished.

U.S. Pat. No. 5,693,856 describes the use of recycled carbon dioxide as a flammability suppressor in a terephthalic acid producing reactor. No mention is made with regard to the amount of $CO_2$ to be added to the reactor and, compared to using nitrogen, the described process does not reduce the flow of inerting gas.

U.S. Pat. No. 5,552,131 describes a highly specialized reactor design and an elaborate way of adding $O_2$ to the reactor liquid phase for a particular reaction. A ballast gas (methane, ethane and propane) is added to the product stream to avoid flammability problems. Again, the amount of the ballast gas to be added is not discussed.

One problem not addressed by the prior art is the fact that any supplemental inerting gas added to the liquid phase process must be treated with the off-gas. Typically, the use of such additional inerting gas disadvantageously raises the off-gas treatment costs and increases the required equipment sizes. Thus, it would be desirable to provide additional inerting gas without raising off-gas treatment costs.

Specifically, in order to handle the additional gas, reactor condensers, separation equipment, and vent gas treatment equipment must be larger. Process utilities such as cooling water, steam, electricity, and fuel for the incineration of waste gases are also increased when supplemental inert gas is used.

Accordingly, it is an object of this invention to provide a method of reducing the amount of inert gas required to render the liquid phase reaction reactor headspace nonflammable.

SUMMARY OF THE INVENTION

In one aspect, the present invention is directed to a method for minimizing a molar flow of an inerting gas effective to prevent combustion, deflagration, or detonation in a headspace of a liquid phase reaction reactor, wherein the liquid phase reaction includes a flammable process liquid and molecular oxygen. The method comprises the following steps:

A) Introducing to the liquid phase reaction reactor an inerting gas effective to form a gaseous mixture in the headspace, wherein the gaseous mixture comprises the inerting gas, a vapor of the flammable process liquid and the molecular oxygen. The inerting gas has a boiling point lower than the flammable process liquid boiling point. The gaseous mixture has a limiting oxygen value higher than the corresponding limiting oxygen value for a mixture of nitrogen, the flammable process liquid vapor and oxygen.

B) Maintaining an amount of the inerting gas in the liquid phase reaction reactor effective to ensure that the headspace remains outside the flammability region.

In another aspect, the present invention is directed to a process to carry out a liquid phase reaction requiring molecular oxygen, while minimizing the required molar flow of inerting gas, comprising:

A) adding a flammable process liquid to a liquid phase reaction reactor having a liquid reaction phase and a headspace;

B) adding molecular oxygen to the liquid phase reaction reactor;

C) adding to the liquid phase reaction reactor an inerting gas other than, or in addition to, nitrogen effective to form in the headspace a gaseous mixture comprising the inerting gas, a vapor of the flammable process liquid and molecular oxygen, wherein the inerting gas has a lower boiling point than the flammable process liquid boiling point, and wherein the gaseous mixture has a higher limiting oxygen value than the limiting oxygen value for a corresponding mixture of nitrogen, the vapor of the flammable process liquid and molecular oxygen;

D) maintaining in the liquid phase reaction reactor an amount of inerting gas effective to ensure that the headspace remains outside the flammability region, said amount being lower than the amount of nitrogen required to maintain the headspace outside the flammability region; and E) carrying out the reaction in the liquid reaction phase.

In another aspect, the invention is directed to a method of increasing the productivity of an air-based liquid phase reaction performed in a liquid phase reaction reactor and minimizing a molar flow of an inerting gas effective to prevent combustion, deflagration, or detonation in a headspace of the liquid phase reaction reactor, wherein the liquid phase reaction includes a flammable process liquid and molecular oxygen, and wherein the molecular oxygen is supplied by an atmospheric composition. The method comprises the following steps:

A) Adding supplemental oxygen to the atmospheric composition effective to form an oxygen enriched air composition.

B) Introducing to the liquid phase reaction reactor an inerting gas effective to form a gaseous mixture in the headspace. The gaseous mixture comprises the inerting gas, a vapor of the flammable process liquid, and the molecular oxygen. The inerting gas has a boiling point lower than the flammable process liquid boiling point, and the gaseous mixture has a limiting oxygen value higher than the limiting oxygen value for a corresponding mixture of nitrogen, the flammable process liquid vapor and oxygen.

C) Maintaining an amount of the inerting gas in the liquid phase reaction reactor effective to ensure that the headspace remains outside the flammability region.

According to the present invention, the amount of a ballast gas needed, to prevent combustion, deflagration, and/or detonations during a liquid phase reaction of molecular oxygen and a flammable process liquid, is reduced by using a ballast gas other than just nitrogen. The ballast gas is selected to have a boiling point lower than the boiling point of the flammable process liquid and selected to produce a higher limiting oxygen value (LOV) in a mixture with the flammable process liquid vapor and molecular oxygen than the LOV for the corresponding mixture substituting just nitrogen for the inerting gas.

As used herein, the terms "process gas" and "process liquid" refer respectively to a gas or liquid present in the reactor. A process gas or liquid may be a reacting compound or a solvent introduced to the liquid-phase reactor or it may be one of the reaction products or by-products formed in the reactor.

The terms "inerting gas" or "ballast gas" are used herein interchangeably and refer to a gas, vapor, or a mixture of gases and/or vapors introduced to a liquid-phase oxidation reactor to prevent combustion, deflagration, and/or detonation in the reactor or in the reactor headspace, or feed or evacuation lines.

As used herein, the term "limiting oxygen value" abbreviated as "LOV" refers to the oxygen concentration below which a flame will not propagate in a gaseous mixture containing some form of fuel at a given temperature regardless of the other component percentages of the fuel-oxygen mixture.

As used herein the term "flammable liquid" refers to a liquid or a mixture of liquids capable of being easily ignited and of burning rapidly. Flammable liquids are defined by the National Fire Protection Association (NFPA) and the Department of Transportation (DOT) to have a flash point less than 100° F. (37.8° C.) and a vapor pressure of not over 40 psi (275.8 kPa) at 100° F. (37.8° C.). As used herein, the term "flammable liquid" also includes liquids defined by NFPA as combustible liquids (having a flash point of or above 100° F. (37.8° C.)) which, under the conditions present in the reactor, may take on many of the characteristics of flammable compounds.

DETAILED DESCRIPTION OF THE INVENTION

Figure 1:
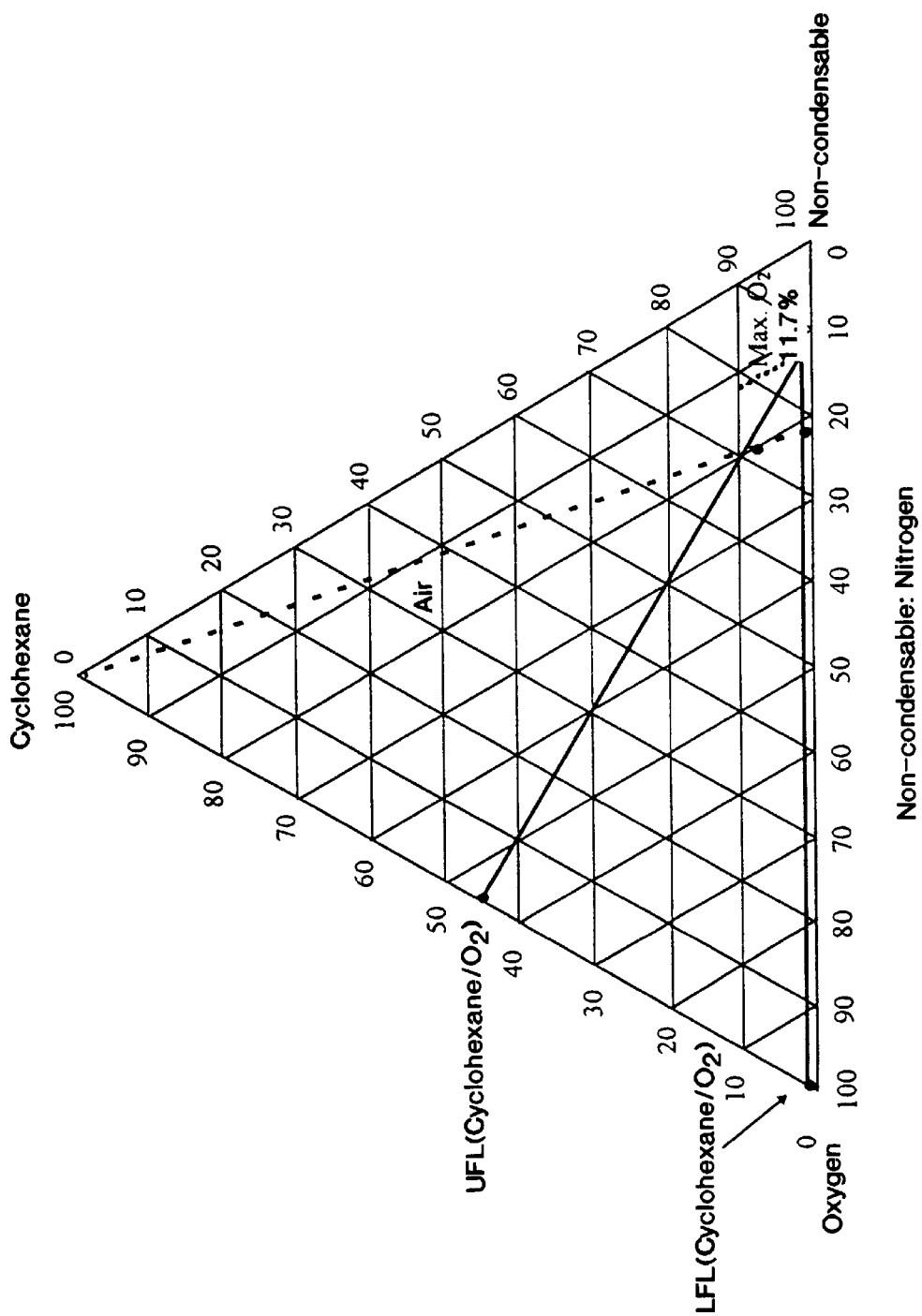
FIG. 1 is a three component phase diagram of a cyclohexane, oxygen, and nitrogen system.
Figure 2:
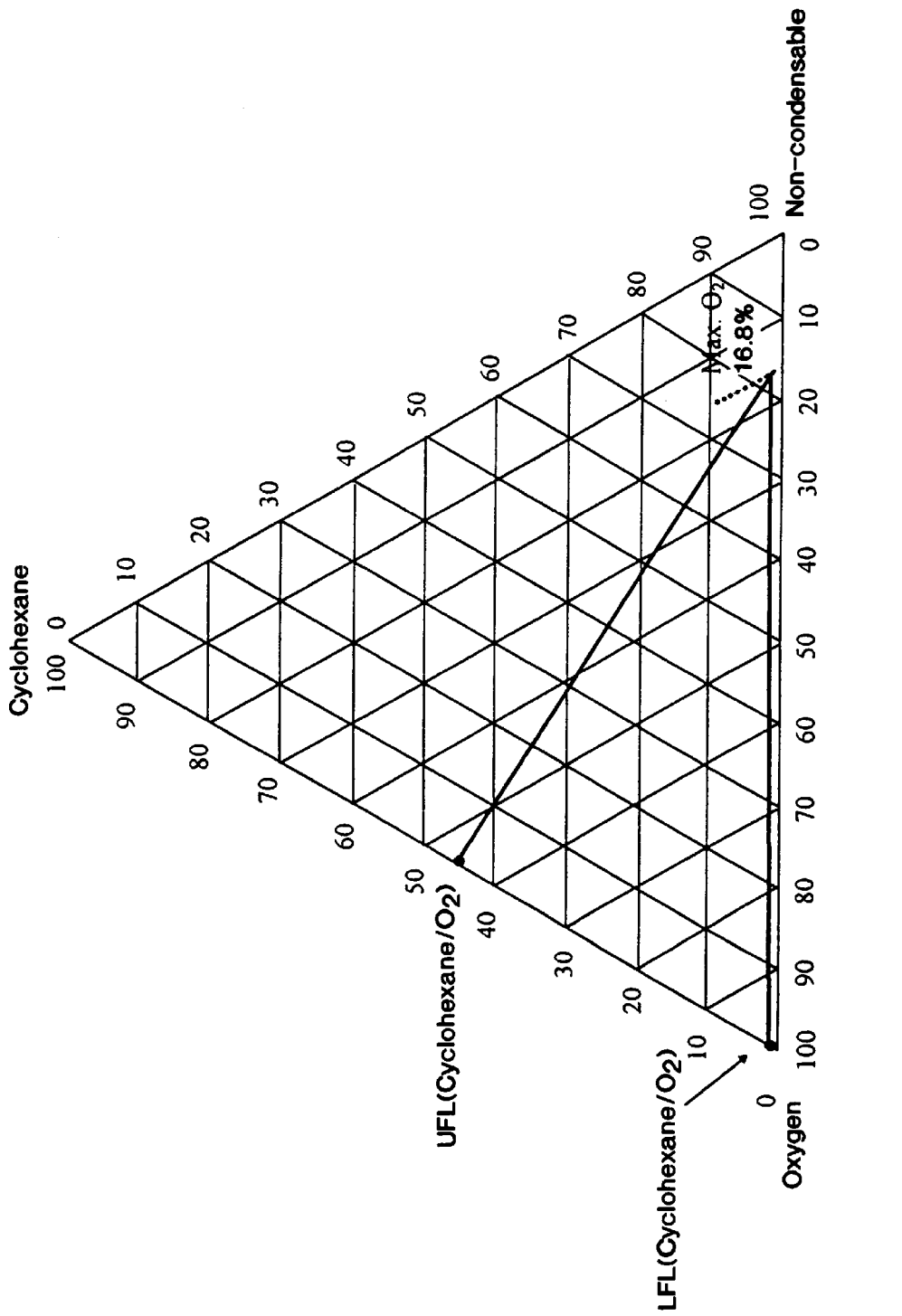
FIG. 2 is a three component phase diagram of a cyclohexane, oxygen, and carbon dioxide system.

The method of the present invention safely carries out a liquid phase reaction involving at least one flammable process liquid and molecular oxygen by using a gas (an "inerting gas") other than nitrogen, or in a mixture with nitrogen, to render inert the headspace of a liquid phase reactor effective to prevent combustion, deflagration or detonation. The method of this invention renders the headspace inert while minimizing the flow of inerting gas. In particular, the method reduces the required flow ("molar flow" generally expressed in mass/unit time, typically moles/hr) of inerting gas when compared with the required flow of just nitrogen for rendering the headspace inert. The flammable process liquid may be the reaction solvent, one of the reacting compounds fed to the reactor or one of the products formed during the chemical reaction.

The molecular oxygen may be provided to the reactor in the form of a gas having greater than or eqaul to about 21 vol. % oxygen. This may be in the form of air, oxygen enriched air (having an oxygen content higher than about 21 volume percent, preferably higher than about 25 volume percent, more preferably higher than about 50 volume percent and most preferably higher than about 85 volume percent) or pure or nearly pure oxygen (e.g. a gas having an oxygen content higher than about 99 volume percent).

The invention is particularly useful in carrying out liquid phase oxidation reactions in liquid phase reactors. Any convenient liquid phase reactor or the Liquid Oxidation Reactor (LOR) can be used to practice the invention such as, for example, those described in U.S. Pat. Nos. 4,900,480, 5,451,349, 5,523,474 or 5,536,875. Typically, a liquid phase reactor has a liquid (reaction) phase and a headspace, with the molecular oxygen process gas generally being added to the liquid phase.

The invention is related to the use of a gas other than nitrogen to inert the headspace of a liquid phase reactor containing a flammable process liquid and molecular oxygen. Nonlimiting examples of inerting gases that may be used to practice the invention include: methane, ethane, other lower alkanes, helium, steam, carbon dioxide and others as long as the selection criteria set forth below are met. Gaseous mixtures may also be used as long as the selection criteria set forth below are met. Gaseous mixtures may include mixtures of nitrogen gas with at least one other inerting gas or vapor.

Since liquid phase reactions typically involve the condensation and recycling of at least one of the process liquids, for example the liquid solvent, the inerting gas must be selected according to the invention in a manner that ensures that the inerting gas will not condense out of the vapor phase before the condensable process liquid. This is a particular concern for inerting gases that have high boiling points such as steam. If this requirement is not met, it is possible that for certain temperature and pressure reactor conditions, the inerting gas may condense before the process vapor and result in a changed composition in the reactor headspace; the increase in the process vapor concentration(s) may thus shift the reactor headspace composition to the flammable regime. Accordingly, the inerting gas is selected to have a boiling point lower than the boiling point of the flammable process liquid.

The inerting gases are also selected in a manner that ensures that the limiting oxygen value (LOV) in the presence of the inerting gas is higher than the LOV when just nitrogen is used to render the headspace inert.

The inerting gas may be a noncombustible gas, for example helium. The inerting gas may also be a combustible gas such as natural gas. Furthermore, the inerting gas may be one of the process gases or vapors, for example carbon dioxide or steam.

The inerting gas may be introduced into the reactor headspace or into the reactor liquid phase. It may be introduced as a mixture with one of the process liquids or process gases or at a separate injection point.

When the inerting gas is a combustible gas, the flammable region determination includes a step of extrapolating to the upper flammability limit and lower flammability limit for a two component mixture of the combustible ballast gas and oxygen. This second extrapolation sets forth the boundary flammable regions of the ternary three component phase diagram caused by the combustible ballast gas. An effective amount of the ballast gas is then added in order to maintain the liquid phase oxidation reactor headspace outside of the flammable region of the three component phase diagram.

As already mentioned, any added supplemental inerting gas must be treated with the reactor off-gas, disadvantageously adding to off-gas treatment costs and increasing equipment sizes. Thus, reduction of vent gas flow would reduce cost. This invention offers advantages in processing and equipment costs that are reduced with respect to conventional nitrogen inerting processes. As a result of the LOV being higher when using the inerting gases disclosed herein than when using just nitrogen, a flow of inerting gas lower than a comparative flow of just nitrogen is required to safely render the reactor headspace nonflammable.

The present invention reduces cost in many other ways. For example, if the replacement inerting gas (flow×cost/volume) is less expensive than nitrogen there will be a savings.

Furthermore, specific processing advantages are gained because the inerting gas may be a fuel already available at the process facility and/or a by-product of the liquid phase reaction.

Treatment of the vent gas from a liquid phase reaction often requires incineration. Such incineration typically requires supplemental fuel (methane, ethane, propane and other gaseous fuels) added to the incinerator in order to fully burn the vent gas. Not only do these fuel gases burn well in the oxygen rich environment of an incinerator, but they can also effectively render inert the oxygen-starved environment typically found in the reactor headspace. As an example, natural gas (chiefly methane) has particularly desirable properties for such double use. According to the invention, rather than feeding it directly to the incinerator, natural gas is first fed to the reactor as a ballast gas and then passed through to the incinerator as a fuel. Consequently, the inerting gas required in the reactor is effectively cost-free since the natural gas was already required in the incineration phase of the process.

Carbon dioxide and/or water (steam) are often co-products in liquid phase oxidation reactions. These process gases also have desirable properties as inerting gases. Therefore, the carbon dioxide and water formed in the primary liquid phase reaction can be recycled and used as inerting gases. Such use of recycled carbon dioxide and water as inerting gas is also effectively cost-free.

The unreacted oxygen that is present in the headspace potentially can be recovered, thereby saving costs. The unreacted oxygen is part of the vent gas that exits from the headspace. By separating the other vent gases from the unreacted oxygen from the reactor, recovered oxygen can be then recycled to the reactor. In this way, the overall utilization of oxygen in a reactor can be nearly 100%, (nearly 100% of the oxygen would be used in the reactor) even though the reactor oxygen conversion efficiency might be less than 100%.

Although such recovery of oxygen does not affect the use of inerting gases of this invention, the choice of an inerting ballast gas can include the consideration of the properties of the inerting gas that would facilitate such oxygen recovery. This invention allows more efficient oxygen recovery because the inerting gases are added in a calculated amount that (i) is easier to separate from oxygen than is nitrogen, (ii) allows increased oxygen concentrations for easier separation, and (iii) allows better facilities calculations for lower capital expenses.

Recycling oxygen offers a number of advantages. First, plant oxygen demand is reduced. For an air-based oxidation, reduced oxygen demand saves on compression energy costs and compression size costs. For an oxygen-based process, reduced oxygen demand saves on the cost of oxygen in the form of energy costs and equipment size costs for the air separation unit used to produce oxygen, and in purchase costs if the oxygen is purchased.

A second advantage is that the reactor can be run at the optimum oxygen utilization by running the liquid phase reaction at excess oxygen conditions. Organic oxidations are often preferably run under excess oxygen to increase reactor productivity and/or product selectively. However, such excess oxygen conditions are typically too costly for use in a "one-pass" oxygen process, because the excess oxygen is just vented away. Such venting of valuable oxygen can make its use, at excess levels, uneconomical. By recovering oxygen, the cost of oxygen is fully utilized and the reactor can be operated optimally with respect to its reaction chemistry while also being operated optimally with respect to its oxygen/fuel costs.

Another advantage is that oxygen recovery is accomplished more easily because of the higher oxygen concentrations possible in the presence of an inerting gas that is a better flammability suppressor than nitrogen. It is easier and more economical to separate and recover a component that is at a higher concentration than when that component is at a lower concentration because more mass is recovered for a given separation step and for a given unit of energy expended.

Further, although oxygen can be recovered in a system inerted with nitrogen, the invention provides significant cost savings because oxygen is more easily recovered from inerting gases disclosed in this invention. For example, oxygen is more easily recovered from steam, because the steam is easily separated from the oxygen by the simple condensation of steam as water.

Figure 5:
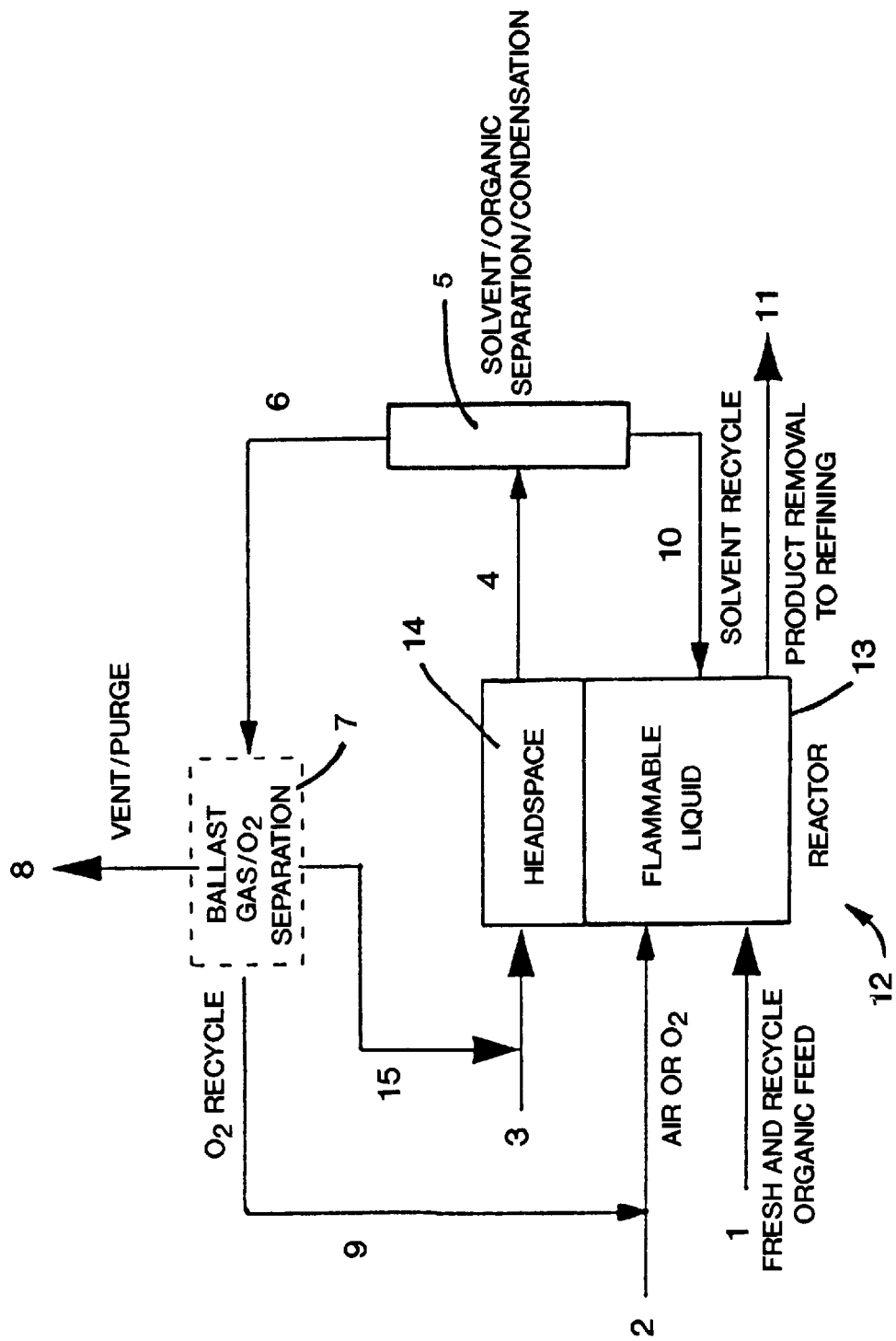
FIG. 5 is a schematic diagram of process involving a liquid phase reactor which may be used in the practice of this invention.

A liquid-phase oxidation process that may be used to practice this invention is shown in FIG. 5. According to the embodiment of FIG. 5, a liquid phase reactor 12 has a liquid phase reaction zone 13 where the oxidation reaction is carried out. Liquid phase reaction zone 13 contains a flammable process liquid. A feedstream 2 of air or oxygen and a feedstream 1 of fresh and recycled organic feed supply liquid phase reaction zone 13. Product is removed through a product stream 11. If volatile or gaseous reaction product is produced, it can be removed at exit stream 8.

Process gases and vapors of process liquids accumulate in a headspace 14. A feedstream 3 supplies inerting gas to headspace 14. Headspace 14 is vented through exit stream 4. A separation/condensation unit 5 recovers process liquids such as organic feed and/or solvents from the gases and vapors evacuated from headspace 14 through exit stream 4. The separation/condensation unit may include any of the processes typically employed for this purpose: absorption, adsorption, distillation, permeation, fractionated condensation and others. The recovered process liquids are returned to liquid phase reaction zone 13 by way of feedstream 10.

The remaining components, other than the organic feed and/or solvents, from separation/condensation unit 5 are directed by conduit 6 to a ballast gas/oxygen separation unit 7 which recovers oxygen. The separation may be by any of the techniques known to one skilled in the art as suitable to perform the separation: adsorption, condensation, membrane separations and others. The recovered oxygen is recycled to the reactor. In the embodiment of FIG. 5, the recycled oxygen is passed through an oxygen recycle conduit 9 to feedstream 2. However, the recycled oxygen may be fed directly to liquid phase reaction zone 13 or may be mixed with feedstream 1. Ballast gas/oxygen separation unit 7 also recovers ballast gas which is passed through a ballast gas conduit 15 to feedstream 3 and then to headspace 14. As noted above, ballast or inerting gas, whether recycled or fresh, may also be mixed with one of the process liquids or process gases fed to the reactor or it may be injected into the reaction zone or the reactor headspace. Waste product is vented/purged at exit stream 8.

The invention is widely applicable to liquid phase oxidation reactions. Nonlimiting examples include the oxidation reactions of ortho-, meta- or para-xylenes, the oxidation of toluene or para-toluic aldehyde and of other similar aromatic compounds, the liquid phase oxidation of ethylene to obtain acetaldehyde, the reaction of aliphatic aldehydes to produce aliphatic carboxylic acids (for example by the Low Pressure Oxo Process), liquid phase oxidation reactions to produce caprolactam, phenol, adipic acid and others.

Below, the invention is described in further detail with respect to one illustrative liquid phase process: the oxidation of cyclohexane to cyclohexanone. For simplicity, only two reactions are discussed. Side reactions or the actual cyclohexane conversion levels in existing processes will be ignored as their consideration only adds to the scaling of the gas requirements to account for the added cyclohexane feed, as would be apparent and understood upon examination of the calculations described below. For the following discussion and examples, the cyclohexane feed is consumed fully. The process involves a main reaction, the oxidation of cyclohexane to cyclohexanone:

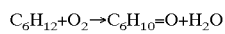

and a secondary reaction, the combustion of cyclohexane to carbon dioxide and water.

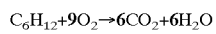

For oxygen-based processes, it is assumed that 99% of the oxygen fed to the reactor is consumed in the reactor. This is consistent with the performance of a liquid phase reactor such as the Liquid Oxidation Reactor described in A. K. Roby and J. P. Kingsley, ChemTech, Vol. 26, No. 2, pg. 39 (1996). Further, it is assumed that 98% of the oxygen consumed is consumed by the main liquid phase reaction and the remaining 2% of consumed oxygen is consumed by the headspace combustion reaction.

Finally, it is assumed that, due to safety considerations, not only headspace 14, but also liquid phase reaction zone 13, as well as separation/condensation unit 5 must be kept below the system LOV since, as the solvent is condensed, the composition in separation/condensation unit 5 might pass through the flammability region even though headspace 14 might remain outside the flammability range. However, the relative ratio of inerting gas to oxygen is fixed as long as the inerting gas is not condensed in separation/condensation unit 5. The conditions in separation/condensation unit 5 are controlled, as would be known to one of ordinary skill, to prevent the condensation of inerting gas.

The examples below can be discussed in terms of FIGS. 1–4 which are ternary flammability diagrams for mixtures of cyclohexane vapor (for short cyclohexane), oxygen, and an inerting gas labeled in the Figures as "non-condensable". (As already discussed, it is assumed that the inerting gas is not condensed in the separation/condensation unit 5). For FIGS. 1–4, the inerting gas is nitrogen, carbon dioxide, water, and methane, respectively.

The ternary flammability diagrams presented in the Figures were constructed from flammability data available in the literature and predictions using extrapolations from flammability data for other hydrocarbons and published models. The figures illustrate the increase in the limiting oxygen value (LOV) when nitrogen is replaced by other inerting gases according to this invention.

In each of the figures, the bottom base scale represents the percent of oxygen in the three component mixture, with the left bottom corner of the triangle representing 100% oxygen. The left side of the triangle represents the percent of cyclohexane, the top corner of the triangle representing 100% cyclohexane. Finally, the right side of the triangle represents the percent of non-condensable (inerting gas) in the three component mixture, with the bottom right corner of the triangle representing 100% non-condensable. Unless specifically stated otherwise, percentages used herein are by volume.

FIGS. 1–4 can also be described as having the bottom triangle side being the oxygen/non-condensable axis, the right side of the triangle being the cyclohexane/non-condensable axis, and the left side of the triangle being the cyclohexane/oxygen axis. Any point within the triangle defines a particular composition of % oxygen/% cyclohexane/% non-condensable, with any particular composition adding to 100%.

The following discussion shows how the region of flammability for mixtures of cyclohexane and oxygen in nitrogen, carbon dioxide, water, or methane inerting gas, referred in this discussion as non-condensable, can be calculated in order to determine the process conditions. Generally, the effect on the lower flammability limit (LFL) of adding a non-condensable to a fuel/$O_2$ mixture (in this case cyclohexane/oxygen mixture) is negligible. Thus, for liquid phase oxidation reactions having limited available data, the effect to the LFL of adding the ballast gas can be neglected. This assumption is consistent with the data available in the literature. See, for example, B. Lewis and G. von Elbe, "Combustion, Flames and Explosions of Gases", 3rd Ed., Academic Press (1987); J. G. Hansel et al., Plant/Operations progress, vol 11, no. 4, pp. 213–217.

For these examples, the upper (UFL) and lower (LFL) flammability limits of cyclohexane in air and in pure oxygen, and the UFL and LFL of methane in pure oxygen, were obtained from H. F. Coward and G. W. Jones, Bureau of Mines, Bulletin 503 (1952). For other flammable process liquids and ballast gas systems, if the UFL and LFL of the two component system are not known, it is a simple and well known procedure to determine their values experimentally.

The elbow on a typical ternary flammability diagram (see FIG. 1, for example) represents what is referred to as the maximum safe percentage of oxygen (LOV) because it is the oxygen percentage below which no mixture of combustible and inert gas will ignite. Although published data is not available for the LOV of cyclohexane in any of these diluents, it can be predicted using the model of Subramaniam and Cangelosi. (T. K. Subramaniam, J. V. Cangelosi, J. Chemical Engineering, December, 108–113 (1989), incorporated herein by reference.

Subramaniam and Cangelosi have developed a group contribution technique which was effective in predicting the LOV for hydrocarbon/oxygen/nitrogen mixtures at ambient temperature and pressure. In this technique, the stoichiometric number of oxygen moles ($O_S$) required to completely burn 1 mole of combustible gases is calculated, followed by a determination of the number of moles of nitrogen ($N_T$) necessary to dilute the stoichiometric moles of oxygen to the maximum safe percentage oxygen. The model is able to successfully correlate the total nitrogen requirement per mole of combustible ($N_T$) using group nitrogen contributions for a wide range of substances. The LOV is then calculated from the following equation (1):

$$O_{max\%} = \frac{100\, O_s}{(1 + O_S + N_T)} \quad (1A)$$

Equation (1A) therefore can be generalized to determine the maximum safe percentage of oxygen (LOV) for a given ballast gas, X, according to the following generalized equation (1)

$$LOV = 100 O_S/(1+O_S+N_X) \quad (1)$$

where $O_S$, is the stoichiometric number of oxygen moles required to completely burn 1 mole of the combustible gas and $N_X$ is the number of moles of the ballast gas, X, required to dilute $O_S$ moles of oxygen to a safe level. $N_X$ is determined by the following equation (2):

$$N_X = N_T(C_P^{N_2}/C_P^X) \quad (2)$$

where $N_T$ is the number of moles of nitrogen required to dilute $O_S$ moles of oxygen to a safe level, $C_P^{N_2}$ is the average heat capacity of nitrogen, and $C_P^X$ is the average heat capacity of the ballast gas.

This approach is used to construct the flammability characteristics of cyclohexane and oxygen in nitrogen, carbon dioxide, water, and methane described below.

Nitrogen

Referring to FIG. 1, the cyclohexane/$O_2$/$N_2$ ternary flammability diagram was constructed using published flammability data for cyclohexane in air as described in H. F. Coward and G. W. Jones, Bureau of Mines, Bulletin 503 (1952)) and pure oxygen as described in S. Crescitelli, G. DeStefano, G. Russo, and V. Tufano, J. Hazardous Materials, Vol. 5, pgs. 177–187 (1982), the disclosure of each of which is incorporated herein by reference. These points are indicated on the diagram. The maximum safe oxygen concentration for this mixture was calculated using the technique of Subramaniam and Cangelosi and was approximately 11.71% (maximum $O_2$ line shown in FIG. 1). In this case, no significant safety factor has been factored in (the maximum $O_2$ value has been multiplied by a safety factor of 1.0).

Linear extrapolation through the UFL and LFL points in air and pure oxygen to the maximum safe percentage oxygen concentration line provides a good representation of the flammable region. The extrapolation was performed by constructing a constant cyclohexane line (the "LFL constant line") from the LFL point of the cyclohexane/oxygen axis to the maximum $O_2$ line. This LFL constant line is one boundary of the flammable region. A line (the "UFL to max$O_2$ line") is then drawn from the UFL point of the cyclohexane/oxygen axis to the point on the maximum $O_2$ line where the previously drawn LFL constant line intersects. The flammable region is bound by the LFL constant line, the UFL to max$O_2$ line, and the cyclohexane/oxygen axis between the LFL and UFL points.

Carbon Dioxide

There is very little published data for the flammability of cyclohexane/$O_2$/$CO_2$ mixtures. In order to calculate the LOV of this mixture, data for the effect of $CO_2$ addition on the LOV of other hydrocarbons was examined from, for example, Lewis and von Elbe. For a range of hydrocarbons (methane, ethane, propane, butane, ethylene, propylene, cyclopropane, butadiene, benzene, hexane, methanol, and ethanol), the LOV appeared to correlate well with the extent of $N_2$ reduction. On average, a 46% (±3.8) reduction in nitrogen (on an oxygen basis) led to a 22% (±3) increase in the LOV. Linear extrapolation to 100% replacement of nitrogen with $CO_2$ gives an LOV of approximately 17.5% for a cyclohexane/$O_2$/$CO_2$ mixture.

The model of Subramaniam and Cangelosi was extended to predict the LOV of a mixture containing cyclohexane, $O_2$, and a non-condensable other than nitrogen. The change in the flammability characteristics of a gaseous mixture upon addition of an inerting material is related to the change in the average heat capacity of the mixture. Taking this factor into account, $N_T$ was converted into $N_{CO_2}$ (the equivalent number of moles of $CO_2$) by applying their respective average heat capacities ($C_P$) to the following equation (2A), which is a specific application of equation (2) above:

$$N_{CO_2} = N_t \left( \frac{C_P^{N_2}}{C_P^{CO_2}} \right) \quad (2A)$$

where $C_P^{N_2}$ is the average heat capacity of nitrogen, and $C_P^{CO_2}$ that of carbon dioxide. This gave an LOV for the cyclohexane/$O_2$/$CO_2$ mixture of 16.8%. Thus, there is reasonable agreement of the calculated value with the empirical value obtained by extrapolation from the data of other hydrocarbons.

Water

Figure 3:
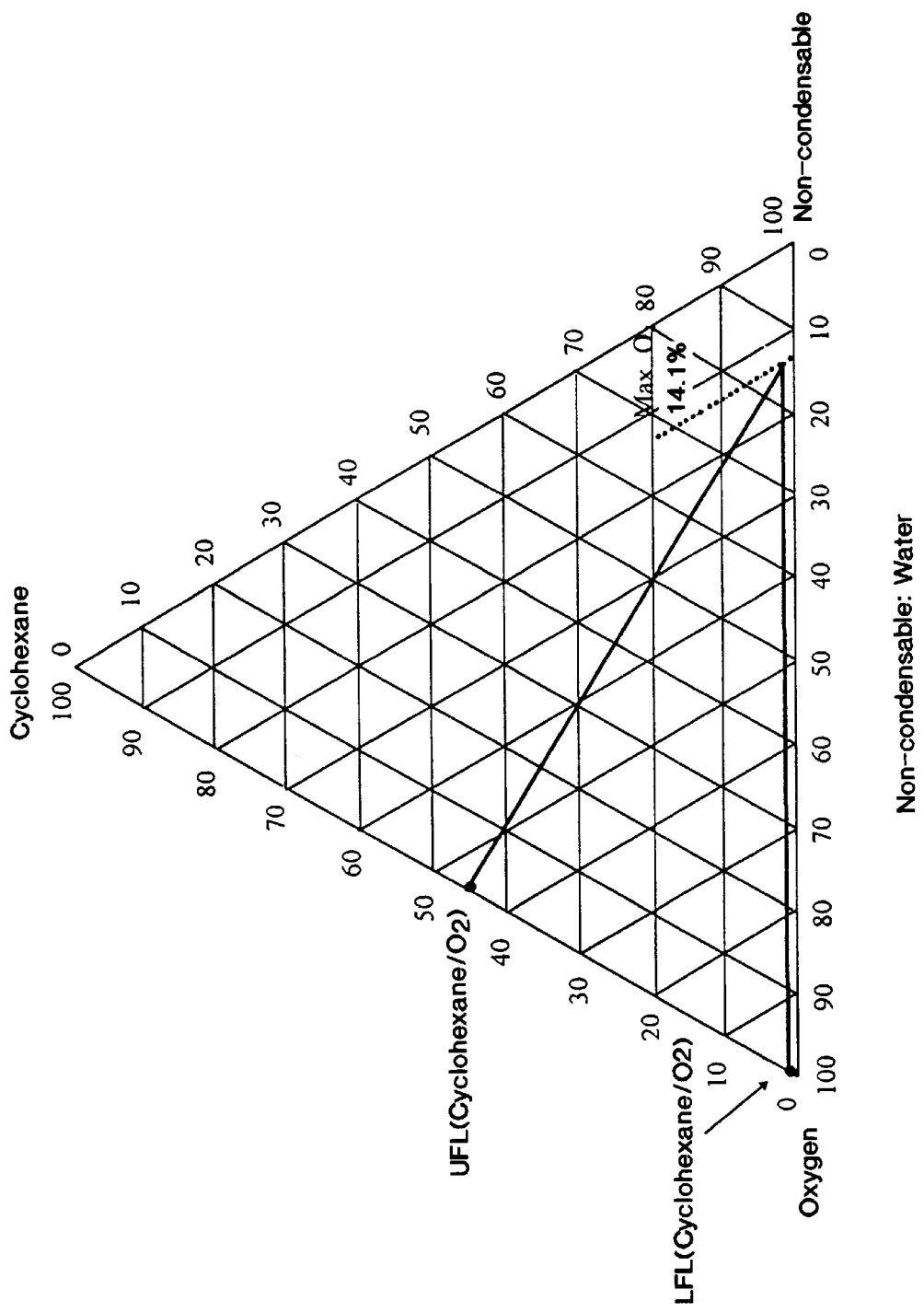
FIG. 3 is a three component phase diagram of a cyclohexane, oxygen, and water system.

The extension of the Subramaniam and Cangelosi model as described above was also used for the cyclohexane/$O_2$/water system. The lack of data on the effect of water on the flammability of hydrocarbons makes an empirical determination difficult without performing experimentation. The calculations resulted in a value of 14.1% for water, which is shown in FIG. 3. (extrapolation from the little data available for the effect of water on the combustion of methane, ethane, and ethanol, M. G. Zabetakis, *Bureau of Mines*, Bulletin 627 (1965)., gave an LOV of 15.3%). The 14.1% LOV value, along with the assumption that the LFL does not significantly change, and linear extrapolation from the UFL point, as described above, produced the flammability diagram for the cyclohexane/$O_2$/$H_2O$ system shown in FIG. 3.

Methane

The cyclohexane/$O_2$/methane system has the added consideration that the non-condensable methane in this case is flammable instead of inert. Therefore, as the concentration of methane drops, rather than approach a non-inflammable mixture of inerts, one moves toward a region of flammability which is defined by the UFL and LFL of a two component methane/$O_2$ system.

Figure 4:
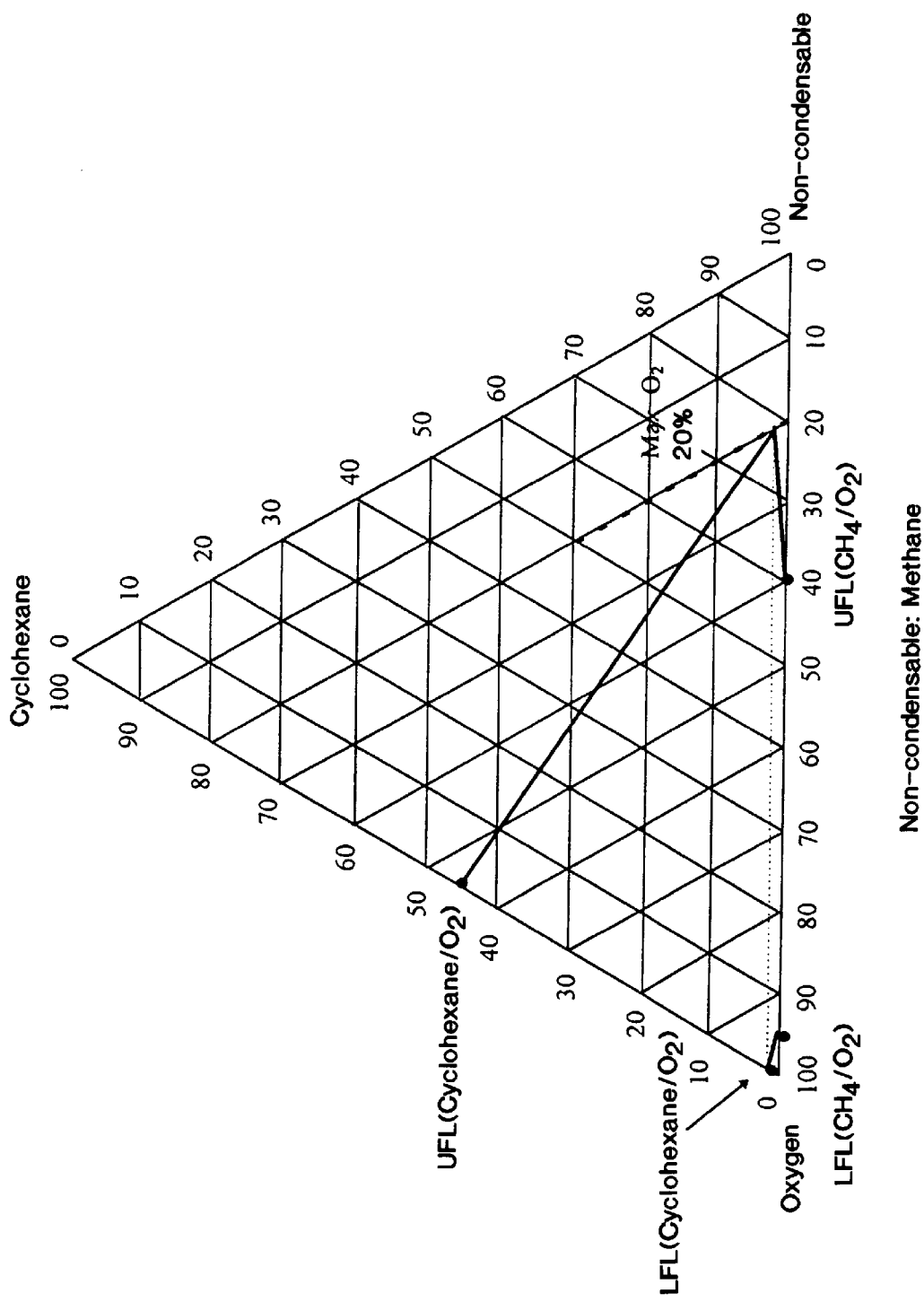
FIG. 4 is a three component phase diagram of a cyclohexane, oxygen, and methane system.

The UFL and LFL of methane in oxygen was obtained from Coward and Jones and are shown in FIG. 4 as points along the bottom two component methane/$O_2$ axis. Determination of the LOV for a mixture of cyclohexane, methane, and oxygen was made using the extension of the Subramaniam and Cangelosi model described earlier, which yielded a value of 20%. This value is probably slightly conservative given the large effect of methane addition on the LOV of a propylene, oxygen, and methane mixture (15% to 40%) described by U.S. Pat. No. 5,430,181. Extrapolation from the pure oxygen data to the maximum oxygen percentage line was performed as described above for the other systems. The flammability of methane in oxygen was accounted for by drawing the lines shown (i) from the LFL point on the cyclohexane/oxygen axis to the LFL point on the methane/oxygen axis, and (ii) from the UFL point of the methane/oxygen axis to the intersection of the UFL to maxO2 line and the Max $O_2$ line. The constructed ternary flammability diagram is shown in FIG. 4 for the cyclohexane/oxygen/methane system with the flammable region indicated.

As described above, the LOV was determined for water, methane, carbon dioxide, and nitrogen as 14.1%, 20%, 16.8%, and 11.7% respectively. As a margin of safety, the values obtained for the maximum safe percentage of oxygen are multiplied by a safety factor. In this case, the factor was chosen as 0.5 to set the target oxygen concentration at half of the determined LOV. Therefore, in the following examples, the headspace will be inerted to an oxygen level of 7%, 10%, 8.5% and 6% for water, methane, carbon dioxide, and nitrogen, respectively.

EXAMPLES

Comparative Example C1

Oxygen-based oxidation of cyclohexane with nitrogen inerting of the headspace. No oxygen recycle or ballast gas recovery (Stream 15 flow =0).

In this system, the LOV is 12%, so the target oxygen value in the headspace is 6%. For 100 mols of cyclohexane feed, 101 mols of oxygen will be required in the reactor. 1 mol of the oxygen will leave in the vent, 99.8 mols of cyclohexane will be produced and, in order to keep the headspace inert, 16 mols of nitrogen will be required. This will lead to 18 mols of vent gas which must be handled by the downstream equipment. The stream flow reference numbers refer to number designations in FIG. 5, and their values are shown below in Table I:

TABLE I

Relative molar flows for Comparative Example C1

| | stream # (mols/hr) | | | | | | |
|---|---|---|---|---|---|---|---|
| | 3 | 15 | 2 | 1 | 9 | 8 | 6 | 11 |
| oxygen | 0.00 | 0.00 | 101.01 | 0.00 | 0.00 | 1.01 | 1.01 | 0.00 |
| cyclohexane | 0.00 | 0.00 | 0.00 | 100.00 | 0.00 | 0.00 | 0.00 | 0.00 |
| cyclohexanone | 0.00 | 0.00 | 0.00 | 0.00 | 0.00 | 0.00 | 0.00 | 99.78 |
| methane | 0.00 | 0.00 | 0.00 | 0.00 | 0.00 | 0.00 | 0.00 | 0.00 |
| water | 0.00 | 0.00 | 0.00 | 0.00 | 0.00 | 0.00 | 0.00 | 1.32 |
| nitrogen | 15.82 | 0.00 | 0.00 | 0.00 | 0.00 | 15.82 | 15.82 | 0.00 |
| carbon dioxide | 0.00 | 0.00 | 0.00 | 0.00 | 0.00 | 1.32 | 1.32 | 0.00 |
| Total flow | 15.82 | 0.00 | 101.01 | 100.00 | 0.00 | 18.15 | 18.15 | 101.10 |

Example 1

Oxygen-based oxidation of cyclohexane with methane inerting of the headspace. No oxygen recycle or ballast gas recovery (Stream 15 flow=0).

As the previous calculations show, the LOV increases from 12% to 20% by using methane instead of nitrogen. Therefore, the target oxygen level in the headspace increases from 6% to 10% because methane is a much more effective efficient flammability suppressor.

For 100 mols of cyclohexane feed, 101 mols of oxygen will be required in the reactor with 1 mol of oxygen leaving in the vent unreacted. 9 mols of methane would be required per 100 mols of cyclohexane processed as opposed to 16 mols of nitrogen required in Comparative Example C1. This is less than 60% of the inert gas required in Comparative Example C1. As a consequence of the lower inert gas flow, the vent gas flow is also reduced from 18 mols to less than 12 mols or about 60% of Comparative Example C1. Table II shows stream flows for Example 1. The methane concentration in the vent is about 90%, safely above the upper flammability limit of methane in oxygen as described in H. F. Coward, G. W. Jones, *Bureau of Mines*, Bulletin 503 (1952).

If the vent stream is to be incinerated, the high concentration of methane can improve incinerator performance. As described above, methane often needs to be added to the vent stream for incineration, particularly for high inert loaded streams. Methane is already provided in the stream. The molar flows in the various flow streams under the reference numbers used in FIG. 5 are shown in Table II below:

TABLE II

Relative molar flows for Example 1 stream # (mols/hr)

|  | 3 | 15 | 2 | 1 | 9 | 8 | 6 | 11 |
|---|---|---|---|---|---|---|---|---|
| oxygen | 0.00 | 0.00 | 101.01 | 0.00 | 0.00 | 1.01 | 1.01 | 0.00 |
| cyclohexane | 0.00 | 0.00 | 0.00 | 100.00 | 0.00 | 0.00 | 0.00 | 0.00 |
| cyclohexanone | 0.00 | 0.00 | 0.00 | 0.00 | 0.00 | 0.00 | 0.00 | 99.78 |
| methane | 9.09 | 0.00 | 0.00 | 0.00 | 0.00 | 9.09 | 9.09 | 0.00 |
| water | 0.00 | 0.00 | 0.00 | 0.00 | 0.00 | 0.00 | 0.00 | 1.32 |
| nitrogen | 0.00 | 0.00 | 0.00 | 0.00 | 0.00 | 0.00 | 0.00 | 0.00 |
| carbon dioxide | 0.00 | 0.00 | 0.00 | 0.00 | 0.00 | 1.32 | 1.32 | 0.00 |
| Total flow | 9.09 | 0.00 | 101.01 | 100.00 | 0.00 | 11.42 | 11.42 | 101.10 |

Example 2

Oxygen-based oxidation of cyclohexane with recovered carbon dioxide inerting of the headspace.

By using carbon dioxide instead of nitrogen, the LOV increases from 6 to 17%, so the target oxygen level in the headspace increases from 6% to 8.5%. For 100 mols of cyclohexane feed, 101 mols of oxygen will be required in the reactor with 1 mol of oxygen leaving in the vent unreacted. Carbon dioxide is recovered from the stream by condensation or adsorption, and returned to the headspace. In this example, the $CO_2$ recovery system is run at 90% $CO_2$ recovery. By operating in this manner, more than the amount of $CO_2$ required for headspace inerting is produced in the reactor by the combustion side-reaction, and no inert gas is required to be fed to the process.

In this example, the vent gas from the solvent recovery system is about 13 mols for every 100 mols of cyclohexane fed as compared to 18 mols for Comparative Example C1 or 72% of Comparative Example C1. However, because of the inert gas recovery, the vent gas that leaves the reactor loop is only the unreacted oxygen and carbon dioxide formed by the burn reaction that must be purged. This is a total of 2.3 mols per 100 mols of cyclohexane processed compared to 18 mols in Comparative Example C1, or 13% of Comparative Example C1. In this scenario with 90% $CO_2$ recovery, the design criteria of maintaining oxygen below 8.75% in stream 6 (50% of the LOV) is actually exceeded, as the resulting oxygen concentration in stream 6 is 7.6%. The molar flows in the various flow streams under the reference numbers used in FIG. 5 are shown in Table III below:

Example 3

Oxygen-based oxidation of cyclohexane with methane inerting of the headspace and methane and oxygen recovery.

As in Example 1, the LOV for methane is 20% and the target level of oxygen will be 10%. The vent gas flows to the condenser (Stream 6) is the same as in Example 1, 11.4 mols per 100 mols of cyclohexane feed (60% of Comparative Example C1). However, because the methane and unreacted oxygen are recovered, only 1.3 mols of $CO_2$ formed in the combustion side-reaction leave the reactor loop (Stream 9). This is less then 8% of the vent gas in Comparative Example C1. The methane requirement is only the amount required to initially charge the reactor loop, and the overall plant utilization of oxygen is 100%, even though the oxygen utilization in the reactor is only 99%.

Oxygen recovery can provide flexibility. As discussed above, it is often advantageous to feed a reactor with excess oxygen to assure that there are no regions in the reactor which are oxygen deficient. Among the disadvantages, oxygen deficiency is often associated with selectivity losses to coupled by-products and increased solvent burn rate. However, in standard processes, the unreacted oxygen is vented, and more fresh inerting gas is required. This is often costly. By recycling the inerting gas and the oxygen, however, no additional fresh inerting gas is required, and the unreacted oxygen is recycled and eventually used. This still requires the same amount of vent gas to be processed in the solvent recovery column, but the amount of raw materials is no larger than that needed for a high oxygen utilization process. Finally, the vent gas that leaves the reactor loop (Stream 8) is still unchanged, and may even be reduced if the burn rate is reduced due to the higher oxygen concentration

TABLE III

Relative molar flows for Example 2

Stream # (mols/hr)

|  | 3 | 15 | 2 | 1 | 9 | 8 | 6 | 11 |
|---|---|---|---|---|---|---|---|---|
| oxygen | 0.00 | 0.00 | 101.01 | 0.00 | 0.00 | 1.01 | 1.01 | 0.00 |
| cyclohexane | 0.00 | 0.00 | 0.00 | 100.00 | 0.00 | 0.00 | 0.00 | 0.00 |
| cyclohexanone | 0.00 | 0.00 | 0.00 | 0.00 | 0.00 | 0.00 | 0.00 | 99.78 |
| methane | 0.00 | 0.00 | 0.00 | 0.00 | 0.00 | 0.00 | 0.00 | 0.00 |
| water | 0.00 | 0.00 | 0.00 | 0.00 | 0.00 | 0.00 | 0.00 | 1.32 |
| nitrogen | 0.00 | 0.00 | 0.00 | 0.00 | 0.00 | 0.00 | 0.00 | 0.00 |
| carbon dioxide | 0.00 | 10.91 | 0.00 | 0.00 | 0.00 | 1.28 | 12.19 | 0.00 |
| Total flow | 0.00 | 10.91 | 101.01 | 100.00 | 0.00 | 2.29 | 13.20 | 101.10 | in the reactor. The molar flows in the various flow streams under the reference numbers used in FIG. 5 are shown in Table IV below:

TABLE IV

Relative molar flows for Example 3 stream # (mols/hr)

| | 3 | 15 | 2 | 1 | 9 | 8 | 6 | 11 |
|---|---|---|---|---|---|---|---|---|
| oxygen | 0.00 | 0.00 | 100.00 | 0.00 | 1.01 | 0.00 | 1.01 | 0.00 |
| cyclohexane | 0.00 | 0.00 | 0.00 | 100.00 | 0.00 | 0.00 | 0.00 | 0.00 |
| cyclohexanone | 0.00 | 0.00 | 0.00 | 0.00 | 0.00 | 0.00 | 0.00 | 99.78 |
| methane | 0.00 | 9.09 | 0.00 | 0.00 | 0.00 | 0.00 | 9.09 | 0.00 |
| water | 0.00 | 0.00 | 0.00 | 0.00 | 0.00 | 0.00 | 0.00 | 1.32 |
| nitrogen | 0.00 | 0.00 | 0.00 | 0.00 | 0.00 | 0.00 | 0.00 | 0.00 |
| carbon dioxide | 0.00 | 0.00 | 0.00 | 0.00 | 0.00 | 1.32 | 1.32 | 0.00 |
| Total flow | 0.00 | 9.09 | 100.00 | 100.00 | 1.01 | 1.32 | 11.42 | 101.10 |

Example 4

Increase of reactor throughput by methane/oxygen enrichment of an air-based oxidation.

It has been known in the prior art that reactor productivity of an air-based process can be improved by adding oxygen to the air stream without adding methane. In the present invention, however, this higher productivity can be further taken advantage of by concurrently increasing the organic feed rate, and by using oxygen enrichment to meet the oxygen requirement. For example, by enriching air to 25% oxygen, the organic feed can be increased by 20% with virtually no increase in gaseous feed and vent gas flow rates. Practically, this means that there are no increased compressor requirements and little increased gas loading in the reactor.

This invention, by using additional methane in conjunction with the additional oxygen, differs from conventional oxygen enrichment because the methane alters the inerting requirements of the headspace by increasing the LOV. Thus, while adding just oxygen or just methane only moves the compositional make-up of the reactor headspace along one axis—the oxygen or methane axis—of the phase diagram, adding a combination of methane/oxygen moves the composition across the two dimensional plane of both axes. This has significant beneficial effects over conventional oxygen enrichment processes.

One of the beneficial effects is related to the increased productivity at lower operating temperatures.

In air-based as well as in conventional oxygen enrichment, the inerting requirement is met by the nitrogen carried in with the air stream; typically, no additional nitrogen is supplied to the reactor headspace. While the LOV is the same for both the air-based and the conventional oxygen enrichment case, the oxygen conversion percentage must be higher for the conventional enrichment case (typically having an oxygen concentration of 25% by volume), since, compared to the air-based process (typically having an oxygen concentration of only 21% by volume), more oxygen is provided to the system and more must be consumed to reach the LOV. Generally, in order to consume the additional oxygen, the temperature must be increased.

By practicing this invention, however, oxygen enrichment is associated with a lower percentage conversion of oxygen because the LOV is higher. Consequently, much less, and often, no temperature increase is necessary. Lower temperature operation gives greater control over selectivity and generally minimizes the formation of undesirable by-products.

A second benefit is related to the higher oxygen concentration available throughout the reactor.

In conventional oxygen enrichment the oxygen concentration must be reduced from the enriched oxygen level (typically 25%) to the same LOV as the air-based process. However, by using an alternative inerting gas, the oxygen concentrate is higher throughout the reactor. This leads to higher reaction rates, which may allow a temperature reduction and increased selectivity.

Other variations and modifications of this invention will be apparent to those skilled in this art after careful study of this application. This invention is not to be limited except as set forth in the following claims.

What is claimed is:

1. A method for minimizing a molar flow of an inerting gas effective to prevent combustion, deflagration, or detonation in a headspace of a liquid phase reaction performed in a liquid phase reaction reactor, wherein said liquid phase reaction includes a flammable process liquid and molecular oxygen, said method comprising:

introducing to said liquid phase reaction reactor an inerting gas such that a gaseous mixture comprising said inerting gas, a vapor of said flammable process liquid, and said molecular oxygen is formed in said headspace, wherein said inerting gas has a boiling point lower than the flammable process liquid boiling point, and wherein said gaseous mixture has a limiting oxygen value higher than the limiting oxygen value for a corresponding mixture of nitrogen, said flammable process liquid vapor and molecular oxygen; and maintaining an amount of said inerting gas in the liquid phase reaction reactor to ensure that the headspace remains outside the flammability region.

2. A method according to claim 1, wherein said inerting gas includes helium, steam, carbon dioxide, an alkane, a mixture thereof, or a mixture thereof with nitrogen.

3. A method according to claim 1, further comprising:

separating the flammable process liquid from the gaseous mixture downstream from the liquid phase reaction, without condensation of the inerting gas; and recycling the separated flammable process liquid to the reactor.

4. A method according to claim 1, further comprising:

recovering a portion of inerting gas from an exit stream from the headspace; and recycling the recovered portion of inerting gas to the reactor.

5. A method according to claim 1, further comprising:

recovering a portion of molecular oxygen from an exit stream from the headspace; and recycling the recovered portion of molecular oxygen to the reactor.

6. A method according to claim 1, wherein said inerting gas is a combustible gas.

7. A method according to claim 6, further comprising:

directing a portion of the combustible gas, from an exit stream of the headspace, to an incineration process.

8. A method according to claim 1, wherein said inerting gas is a process gas.

9. A method according to claim 1, wherein the molecular oxygen is selected from the group consisting of a gas having greater than or equal to about 21% vol. of oxygen.

10. A method according to claim 1, wherein the liquid phase reaction reactor is a liquid oxidation reactor.

11. A process to carry out a liquid phase reaction requiring molecular oxygen, while minimizing a required molar flow of inerting gas, comprising:

adding a flammable process liquid to a liquid phase reaction reactor having a liquid reaction phase and a headspace;

adding molecular oxygen to the liquid phase reaction reactor;

adding to the liquid phase reaction reactor an inerting gas other than, or in addition to, nitrogen such that a gaseous mixture comprising the inerting gas, a vapor of the flammable process liquid and molecular oxygen is formed in said headspace, wherein the inerting gas has a lower boiling point than the flammable process liquid boiling point, and wherein the gaseous mixture has a higher limiting oxygen value than the limiting oxygen value for a corresponding mixture of nitrogen, the vapor of the flammable process liquid and molecular oxygen;

maintaining in the liquid phase reaction reactor amount of inerting gas to ensure the headspace remains outside the flammability region, said amount being lower than the amount of nitrogen required to maintain the headspace outside the flammability region; and carrying out the reaction in the liquid reaction phase.

12. A method according to claim 11, wherein said inerting gas includes helium, steam, carbon dioxide, an alkane, a mixture thereof, or a mixture thereof with nitrogen.

13. A method according to claim 11, further comprising:

separating the flammable process liquid from the gaseous mixture downstream from the liquid phase reaction, without condensation of the inerting gas; and recycling the separated flammable process liquid to the reactor.

14. A method according to claim 11, further comprising:

recovering a portion of inerting gas from an exit stream from the headspace; and recycling the recovered portion of inerting gas to the reactor.

15. A method according to claim 11, further comprising:

recovering a portion of molecular oxygen from an exit stream from the headspace; and recycling the recovered portion of molecular oxygen to the reactor.

16. A method according to claim 11, wherein said inerting gas is a combustible gas.

17. A method according to claim 16, further comprising:

directing a portion of the combustible gas, from an exit stream of the headspace, to an incineration process.

18. A method according to claim 11, wherein said inerting gas is a process gas.

19. A method according to claim 1, wherein the molecular oxygen is selected from the group consisting of a gas having greater than or equal to about 21% vol. of oxygen.

20. A method according to claim 11, wherein the liquid phase reaction reactor is a liquid oxidation reactor.

* * * * *